United States Patent [19]

Shimizu et al.

[11] Patent Number: 4,891,310

[45] Date of Patent: Jan. 2, 1990

[54] METHOD OF CONTROLLING CULTURE

[75] Inventors: Norio Shimizu; Shinichi Fukuzono, both of Hitachi; Nobuko Nishimura, Katsuta; Yoji Odawara, Hitachi; Tomoaki Sumitani, Hachiooji, all of Japan

[73] Assignee: Hitachi, Ltd., Tokyo, Japan

[21] Appl. No.: 843,613

[22] Filed: Mar. 25, 1986

[30] Foreign Application Priority Data

Mar. 25, 1985 [JP] Japan ................................. 60-58480

[51] Int. Cl.$^4$ ............................................. C12Q 3/00
[52] U.S. Cl. .................................... 435/3; 435/240.1; 435/240.2; 435/243; 435/244; 435/252.3; 435/252.33; 435/252.31
[58] Field of Search ................ 435/287, 289, 3, 240.1; 435/240.2, 243, 244, 253

[56] References Cited

U.S. PATENT DOCUMENTS 3,926,737 12/1975 Wilson et al.
4,336,329 6/1982 Hesse et al. .......................... 435/289
4,493,770 1/1985 Moillet ................................ 435/289

FOREIGN PATENT DOCUMENTS 0052890 6/1982 European Pat. Off.

OTHER PUBLICATIONS

Cordonnier et al–Chem. Abst., vol. 91 (1979), p. 54540y.
Patent Abstracts of Japan, vol. 9, No. 233 (C-304) (1956), 19th Sep. 1985; & JP-A-60 91 979 (Hitachi Seisakusho K.K.) 23-05-1985.
Biotech 83: Proceedings of the INternational Conference on the Commercial Applications and Implications of Biotechnology, London, 4th–6th May 1983, pp. 295–306, Online Publications, Northwood UK; T. Sumitani et al., "Automatic Control of Fermentor Using Microcomputer".
Chemical Abstracts, vol. 99, No. 23, 5th Dec. 1983, p. 609, abstract no. 193128y, Columbus, Ohio, U.S.A.; C. L. Cooney et al., "Application of Computer Control to Yeast Fermentation", & Modell Control Biotech. Processes, Proc IFAC Workshop, 1st 1982, 243–251 (1983).
Chemical Abstracts, vol. 85, No. 11, 13th Sep. 1976, p. 413, abstract no. 76311j, Columbus, Ohio, U.S.A.; S. Aiba et al., "Fed Batch Culture of *Saccharomyces cerivisiae*: A Perspective of Computer Control to Enhance the Productivity in Baker's Yeast Cultivation".
Journal of the Institute of Brewing, vol. 83, No. 5, 1977, pp. 317–318, London, GB; A. E. Humphrey, "The Use of Computers in Fermentation Systems".

Primary Examiner—Sam Rosen
Attorney, Agent, or Firm—Antonelli, Terry & Wands

[57] ABSTRACT

A method of controlling culture wherein cells are aerobically cultured to produce metabolite is characterized by adding substrate and/or inducer to the culture broth, judging the endpoint of the growth of the cells and/or the production of the metabolite or terminating the culture under the guidance of a change in the ratio of the first parameter based on the amount of carbon dioxide evolved by the cell culture to the second parameter based on the amount of oxygen consumed by the cell culture. The ratio is a respiratory quotient, for instance.

17 Claims, 9 Drawing Sheets

5'
CTCAAGGCGCACTCCCGTTCTGGATAATGTTTTTTGCGCCGACATCATAA

Taq I
                                                  ↓
CGGTTCTGGCAAATATTCTGAAATGAGCTGTTGACAATTAATCATCGAAC    Hpa I   Rsa I                        Taq I
   ↓  PB  ↓                    SD  ↓    Leader
TAGTTAACTAGTACGCAAGTTCACGTAAAAAGGGTATCGACAATGAAAGC
                                               MetLysAl peptide   Rsa I
           ↓
AATTTTCGTACTGAAAGGTTGGTGGCGCACTTCCTGAAACGGGCAGTGTA
aIlePheValLeuLysGlyTrpTrpArgThrSer

TTCACCATGCGTAAAGCAATCAGATACCCAGCCCGCCTAATGAGCGGGCT

SD      trp E polypeptide
TTTTTTTGAACAAAATTAGAGAATAACAATGCAAACACAAAAACCGACTG
                               MetGlnThrGlnLysProThrG EcoR I
↓
GAATTCTC  3'
lyIleLeu

METHOD OF CONTROLLING CULTURE

BACKGROUND OF THE INVENTION

This invention relates to a method of controlling culture and an apparatus therefor. More particularly, it relates to a method of controlling culture and an apparatus therefor for the efficient production of metabolites such as antibiotics, amino acids, enzyme and physiologically active substances by microorganisms or animal or plant cells.

It has been a usual practice to produce the abovementioned metabolite by microorganisms or animal or plant cells. Most of conventional processes have been carried out batchwise by simply culturing a seed culture in a medium in a culture tank, which would bring about a low productivity.

Thus the inventors have examined culture methods wherein substrate and inducer are added in the course of the cultivation to thereby improve the productivity. There has been reported no industrial studies about the stage of cultivation at which substrate and inducer should be added.

For example, Japanese Patent Laid-Open No. 141796/1983 has disclosed a culture method for the production of a metabolite, i.e. peptide. However, it is not possible to observe the growth of cells continuously, i.e. on-line, in this method. Thus, as a matter of course, the appropriate point for the addition of substrate and/or similar substances is not discussed therein. Japanese Patent Laid-Open No. 125686/1977 has disclosed a method for culture yeasts although it is not intended to produce metabolite. This method comprises feeding a culture broth depending on the total oxygen consumption rate while maintaining the so-called respiratory quotient within a definite range. Therefore a procedure comprising adding substrate(s) and/or similar substances while monitoring a change in the respiratory quotient is not adopted therein.

SUMMARY OF THE INVENTION

It is an object of the present invention to provide a method of efficiently performing cell culture for the production of metabolite in an industrial scale and an apparatus therefor.

The method of the present invention wherein cells are aerobically cultured to produce metabolite is characterized by adding substrate and/or inducer to the culture broth, judging the endpoint of the growth of the cells and/or the production of the metabolite or terminating the culture under the guidance of a change in the ratio of the first parameter based on the amount of carbon dioxide evolved by the cell culture to the second parameter based on the amount of oxygen consumed by the cell culture.

The cell used in the present invention may be either microbial cells, or animal or plant cells. The present invention would bring about a paticurlarly remarkable effect when applied to the culture of genetic recombinant bacterial cells.

In the method of the present invention, the production of metabolite may be carried out either after the cell culture or simultaneously therewith. The latter process is preferable from an industrial viewpoint.

The detection of each parameter and the culture control including on/off control based on the parameters are preferably performed on-line.

A typical ratio based on such a parameter is a respiratory quotient which will be hereinafter referred to as RQ. RQ means a ratio of the amount of carbon dioxide to that of oxygen and is represented by the following equations. That is, RQ can be determined by the following equations where $\Delta O_2$ represents the difference between the oxygen amount in the supply gas and that in the discharge gas, $\Delta CO_2$ similarly represents the difference between the carbon dioxide amount in the supply gas and that in the discharge gas, Q represents the total gas amount and Cell represents the amount of the cells.

$$RQ = \Delta CO_2 / \Delta O_2 \tag{1}$$

$$RQ = Q \cdot \Delta CO_2 / Q \cdot \Delta O_2 \tag{2}$$

$$RQ = (\Delta CO_2 / \text{Cell}) / (\Delta O_2 / \text{Cell}) \tag{3}$$

$\Delta O_2$ and $\Delta CO_2$ in each equation are parameters based on the above data. When a concentration of each constituent in the supply gas is previously known, it is necessary to determined only those in the discharge gas. Further this ratio is not limited by RQ but can be modified in the following manner. For example, ratios such as $RQ^{-1}$, $RQ \times A$ wherein A represents a constant, $RQ \div B$ wherein B is a constant, $\Delta CO_2/(\Delta CO_2 + \Delta O_2)$, $\Delta O_2/(\Delta O_2 + \Delta CO_2)$, $(\Delta CO_2 \times B)/(\Delta O_2 \times A)$ and $(\Delta CO_2 + A)/(\Delta O_2 + B)$ may be applied to the present invention.

It is preferable to add substrate and/or inducer under the guidance of RQ in a period from the initiation of the rise of RQ till right after the termination of its rise.

The second peak of RQ may be usually referred to as a measure for the judgement of the termination of the production of metabolite, so that it is preferable to terminate the culture at this point.

The apparatus of the present invention comprises a culture tank; a gas supply pipe having an opening in the culture tank; a gas discharge pipe; a substrate supply pipe; a first gas meter determining the amount of the gas passing through the gas supply pipe; a first oxygenn analyzer; a second gas meter determining the amount of the gas passing from the upper space in the culture tank to the gas discharge pipe; a second oxygen analyzer, a carbon dioxide analyzer and a computer for inputting signals from each of the meters and analyzers and for outputting signals for on/off control of a conduit from the substrate supply pipe to the culture tank and/or the control of the feeding.

It is to be understood that various instruments other than the abovementioned such as a carbon dioxide analyzer equipped on the gas supply pipe together with the first oxygen analyzer or a tank for adding substrate(s) and another tank for adding inducer(s) may be added to the apparatus of the present invention without departing from the scope thereof. In this case, output signals of the carbon dioxide analyzer should be transmitted to the electronic computer together with those from other meters and analyzers. On the other hand, when the composition, i.e. oxygen and carbon dioxide concentrations, of the supply gas is previously known, e.g., in the case where an oxygen gas cylinder is used, these gas analyzers for the supply gas can be dispensed with so that it is not necessary to input signals from those analyzers to the computer. Such a case is also included in the scope of the present invention. Furthermore it is preferable from the viewpoint of an on-line operation to add substrate(s) and inducer(s) depending on the output from the computer as described above. In this case, it is preferable to add these substances through a pump and/or a valve equipped at each tank or on a conduit from each tank to the culture tank.

DESCRIPTION OF THE PREFERRED EMBODIMENTS

As an first embodiment of the present invention, a culture method for producing β-galactosidase (β-gal) by a genetic recombinant bacterium is described hereunder.

Genetic recombination techniques whereby a large amount of a useful substances is produced by using a host microorganism which retains a complex plasmid prepared by integrating a gene carrying genetic information concerning the production of the useful substance into a vector plasmid of the host microorganism have been recently developed. These techniques have been put into practice in the production of interferon, insulin and similar substances wherein Escherichia coli is used as a host imcroorganism.

However there has been no known method for producing a large amount of a desired product with the use of a genetic recombinant bacterium carrying the desired gene in an industrial scale, so that it has been urgently required to establish a method for efficiently culturing a genetic recombinant bacterium.

In this embodiment wherein a microorganism which harbors or retains a complex plasmid comprising a desired gene, a vector and a promoter in a cell and which is capable of inducing the gene expression is cultured for allowing the microorganism to express the desired gene and collecting a large amount of the product, a substrate and an inducer are simultaneously added when RQ shows a rapid rise during the culture.

As the promoter for expressing the desired gene, there can be used a trp (tryptophan) promoter, a lac promoter (Nature, 281, pp 544-548, 1979), a tac promoter (Proc. Natl. Acad. Sci. USA, 80, pp 21-25, 1983), etc.

Figure 1:
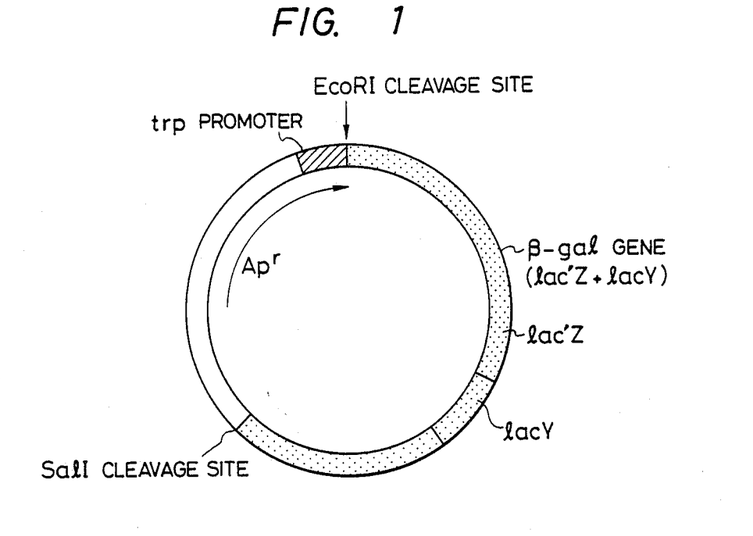
FIG. 1 is a schematic view showing the structure of the complex plasmid pTREZ1.

As the complex plasmid obtained by ligating a trp promoter and β-galactosidase gene, there can be used complex plasmid pTREZ1 having the structure as shown in FIG. 1. The complex plasmid pTREZ1 can be obtained from plasmid pTRE1 and pMC1403.

Figure 2:
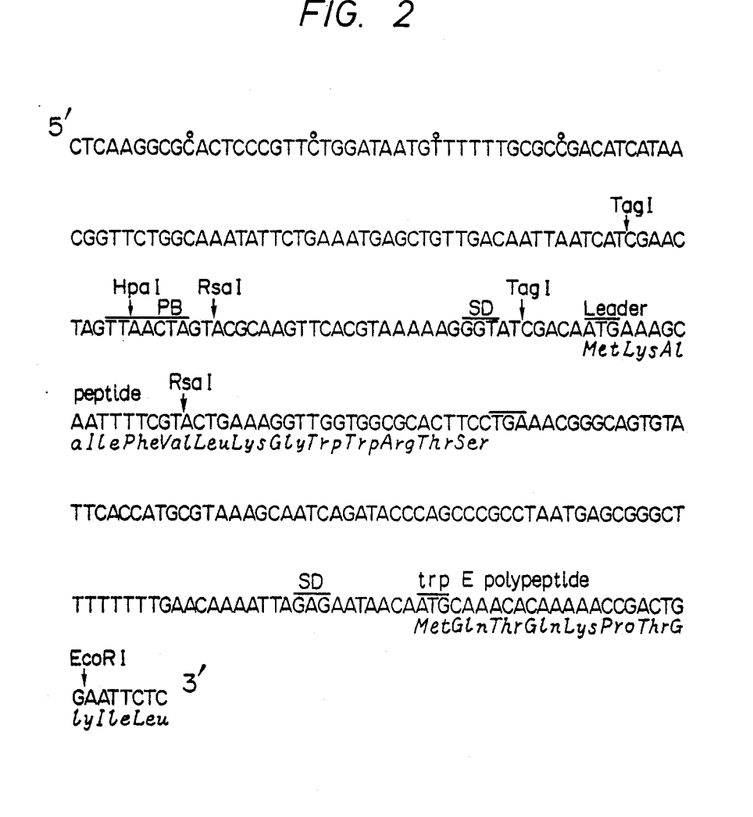
FIG. 2 shows a base sequence at the downstream region of a trp promoter.

The complex plasmid pTRE1 containing a trp promoter is obtained by inserting a DNA fragment of about 500 bp (base pairs) containing a promoter of trp operon of E. coli, trp L (leader peptide) and a part of end portion of trp E (anthranilate synthase) into the EcoRI site of plasmid pBR322 (Gene, 29, pp 41-49, 1984). The direction of trp promoter is the direction of Tc$^r$ (a tetracycline resistance gene) of pBR322. The EcoRI site on the upstream side of trp promoter is lacked by filling up with DNA polymerase I so as to improve only the EcoRI site on the downstream of the promoter. FIG. 2 shows the base sequence in the trp promoter downstream region. By connecting a foreign gene at the EcoRI site in trp E polypeptide gene, it is possible to express the foreign gene in the form fused with 8 amino acids at the N-terminal side of trp E polypeptide.

On the other hand, as the β-galactosidase gene, plasmid pMC1403 (J. Bacteriol, 143, pp 971-980, 1980) can be used. Plasmid pMC1403 is obtained by inserting β-galactosidase gene (lac'Z+lac Y) of 6.2 kb (kilobase pairs) between the EcoRI site and the SalI site of pBR322.

Figure 3:
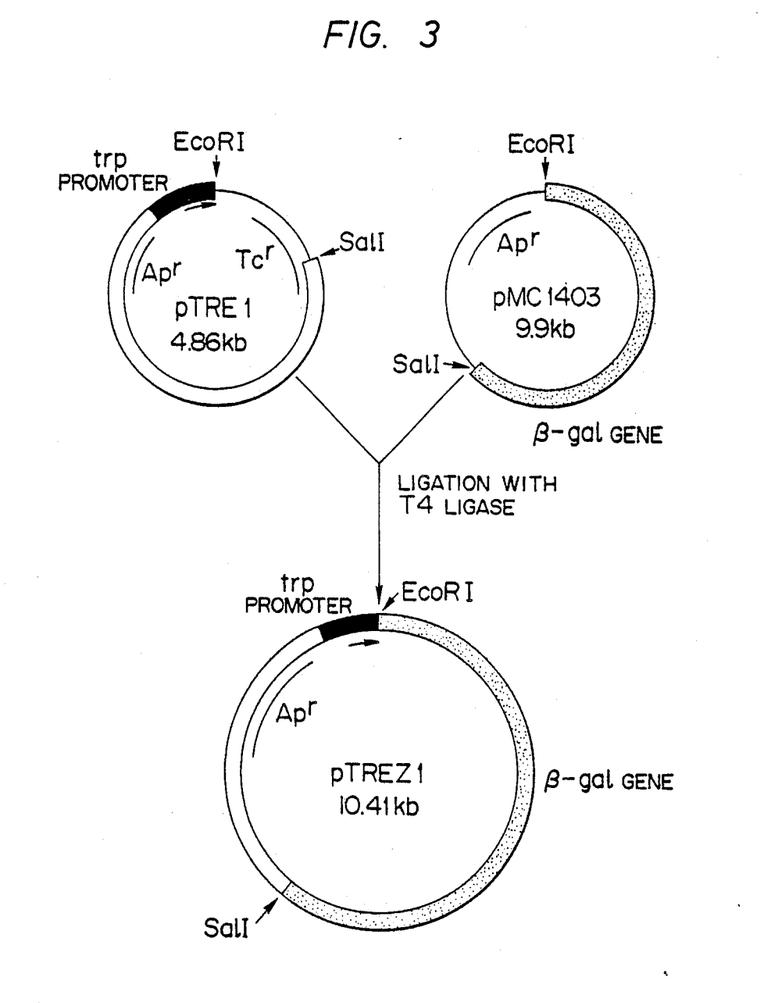
FIG. 3 is a flow diagram showing the construction of complex plasmid pTREZ1.

FIG. 3 shows a process for constructing plasmid pTREZ1 wherein the β-galactosidase gene is connected at the downstream of trp promoter. The complex plasmid pTREZ1 of 10.41 kb can be constructed by ligating the DNA fragment of 4.21 kb containing the trp promoter cut from the plasmid pTRE1 and the β-galactosidase gene of 6.2 kb cut from the plasmid pMC1403 with T$_4$ DNA ligase.

As the microorganism harboring the hydrid plasmid comprising a desired gene, a vector and a promoter in its cell and having the ability to express the desired gene, there can be used various E. coli, e.g. M182, HB101, C600, X1776, DH1, etc. Among them, a recombinant for producing β-galactosidase obtained by introducing the complex plasmid pTREZ1 having the structure mentioned above into E. coli M182 which is a strain lacking in β-galactosidase gene on a chromosome (deposited in the FRI as FERM BP-816) and a recombinant for producing β-galactosidase obtained by introducing the complex plasmid pTREZ1 into E. coli HB101 (deposited in the FRI as FERM BP-815) are under the control of trp promoter and can produce β-galactosidase in a remarkably larger amount than known methods by effectively applying the function of the promoter.

Microorganisms other than E. coli such as yeast, Bacillus subtilis, etc. can also be used as the host microorganism, when suitable promoters are used and desired genes are introduced thereinto.

According to this embodiment, the microorganism containing a complex plasmid comprising a desired gene, a vector to express the desired gene, for example, a microorganism for producing β-galactosidase, is used for expressing the desired gene so as to produce its product, for example, β-galactosidase, with high efficiency. In order to control the culture of the recombinant, the recombinant is supplied to a culture medium for cultivation, and a substrate and/or an inducer are added to the culture medium.

As the inducer, 3-β-indolylacrylic acid (IA) for the trp promoter, isopropyl-β-D-thiogalactoside (IPTG) for the lac promoter and tac promoter, etc. can be used.

As the substrate, there can be used casamino acid which is a mixture of amino acids, glucose, amino acids other than trytophan, yeast extract, and a mixture thereof. Among them, the use of casamino acid is preferable.

It is known that for a complex plasmid having a trp promoter a gene is expressed by adding IA during the cultivation (Nature, 291, pp 503-506, 1981). This is because the repressor suppressing the transcription of genes is inactivated by IA to initiate the synthesis of mRNA by RNA polymerase.

The inventors have studied various methods for controlling culture to thereby efficiently produce β-gal with the use of β-gal-producing genetic recombinant bacteria and consequently succeeded in producing a large amount of β-gal, thus completing the present invention.

The trp promoter starts to function when an inducer IA is added. It is very important in the production of the product of desired gene when the inducer should be added. As to the adding time of IA, a method of the addition at one hour from the beginning of the culture is disclosed in Nature, vol. 291, pp 503–506, 1981 and a method of using the microorganism concentration as an indicator is disclosed in Japanese Patent Laid-Open No. 141796/83. These methods, however, are insufficient for industrial culture.

Figure 4:
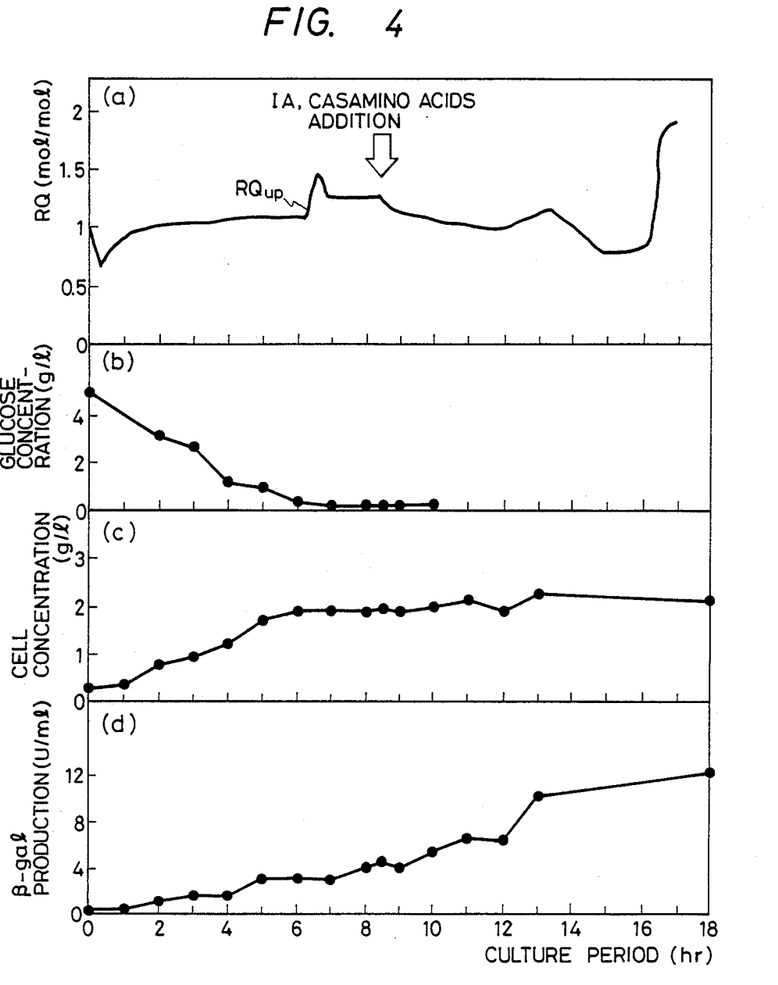
FIG. 4 is a grah showing the relationships among RQ, cell growth and β-gal production.

The inventors have examined the addition of IA in these methods suitable for the physiological state of the strains and found that a change in RQ during the culture closely relates to the growth of the cells and the production of β-gal. The expression "RQ" as used herein means a value determined by dividing the amount of $CO_2$ produced by the cells by the amount of $O_2$ consumed thereby. As shown in FIG. 4, RQ roughly remains constant as 1 mol/mol during the growth of the cells. 6.5 hours after the initiation of the culture when the cell concentration reaches the maximum, RQ rapidly rises to approximately 1.25 mol/mol. At this point, glucose i.e., a substrate is consumed. 8.5 hours after the initiation of the culture, 15 μg/ml of IA which is an inducer and 2.5 mg/ml of casamino acids which are the substrate in the production of β-gal are added at the same time. As a result, the amount of the β-gal produced rises from 4.5 U/ml to 12.3 U/ml 18 hours after the initiation of the culture. After adding IA and casamino acids, RQ returns to approximately 1 mol/mol with showing little growth of the cells. This result suggests that β-gal is produced and accumulated in the cells. A rapid increase in RQ is shown 16.5 hours after the initiation of the culture. It seems that the production of β-gal by the cells is terminated at this point.

Thus it has been revealed that RQ remains constant at 1 mol/mol during the growth of the cells and rapidly rises thereabove when the growth of the cells is terminated, that the cells produce β-gal which is a metabolite when inducer and substrate are added at this point and that RQ is 1 mol/mol at this point and rapidly rises again after the completion of the production of β-gal. Accordingly, efficient mass production of metabolite can be achieved by controlling the culture under the guidance of RQ.

In contrast to this, prior art techniques wherein culture is controlled with the guidance of RQ as disclosed in, e.g., Japanese Patent Laid-Open No. 125686/1977 have disadvantages in that excessive feeding of substrate in feeding culture would result in the formation of ethanol as a by-product, which exhibits an undesirable effect on the growth of the cells, thus bringing about a decrease in the yield of the cells. Since the RQ value exceeds 1 mol/mol in this case to alert to the formation of the ethanol, the feeding of the substrate should be lowered or suspended. In this case, the RQ change is associated with the formation of ethanol unlike in the present invention. In this embodiment, the RQ change is associated with the growth of cells and the production of metabolite. That is, substrates are fed when RQ shows an increase contrary to the case of culturing baker's yeast. In this embodiment, metabolites are efficiently produced by microorganisms or similar cells based on the novel finding that an RQ change during a culture for prorucing metabolite by cells is definitely different from that of culture of baker's yeast.

In this embodiment, glucose and casamino acids may be added at the point when the cells stop growing with an increase in RQ to thereby induce further growth of the cells and continue the culture at an elevated cell concentration and inducer and substrate may be added thereafter. Furthermore additional inducer and substrate such as casamino acids may be added at the point when RQ shows an increase after adding the inducer and substrate to thereby obtain a larger amount of metabolite in the cells.

When the genetic recombinant bacterium carries a promoter for the expression vector other than trp, e.g. lac (lactose) promoter, isopropylthio-β-D-galactoside (IPTG) is employed as an inducer. Production of metabolite by microorganisms other than genetic recombinant bacteria or animal or plant cells may be controlled in the same manner except using different substrate and inducer.

Figure 5:
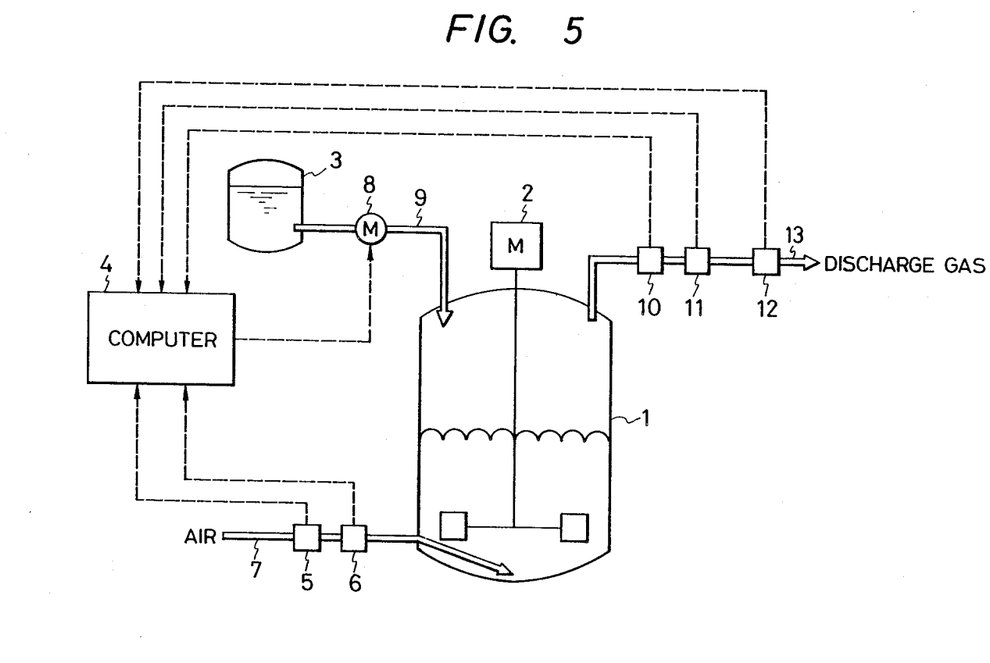
FIG. 5 is a schematic view of an embodiment of the culture control apparatus of the present invention.
Figure 6:
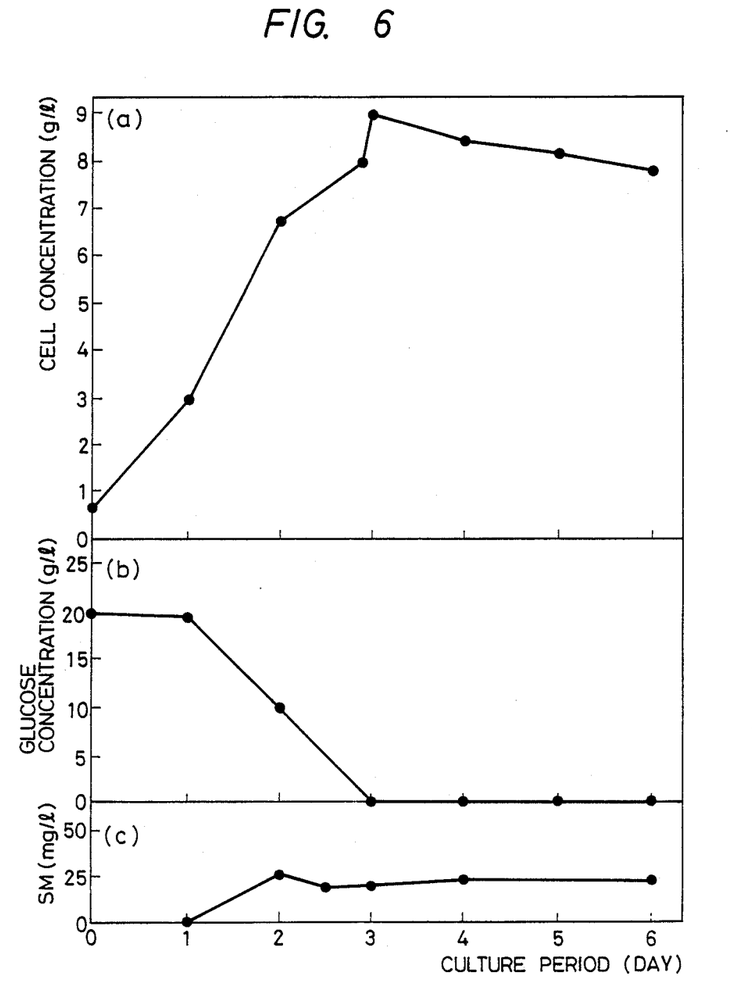
FIGS. 6 and 7 are graphs each showing the result of an SM fermentation test in an automatically controlled culture tank of 50 l in volume.
Figure 7:
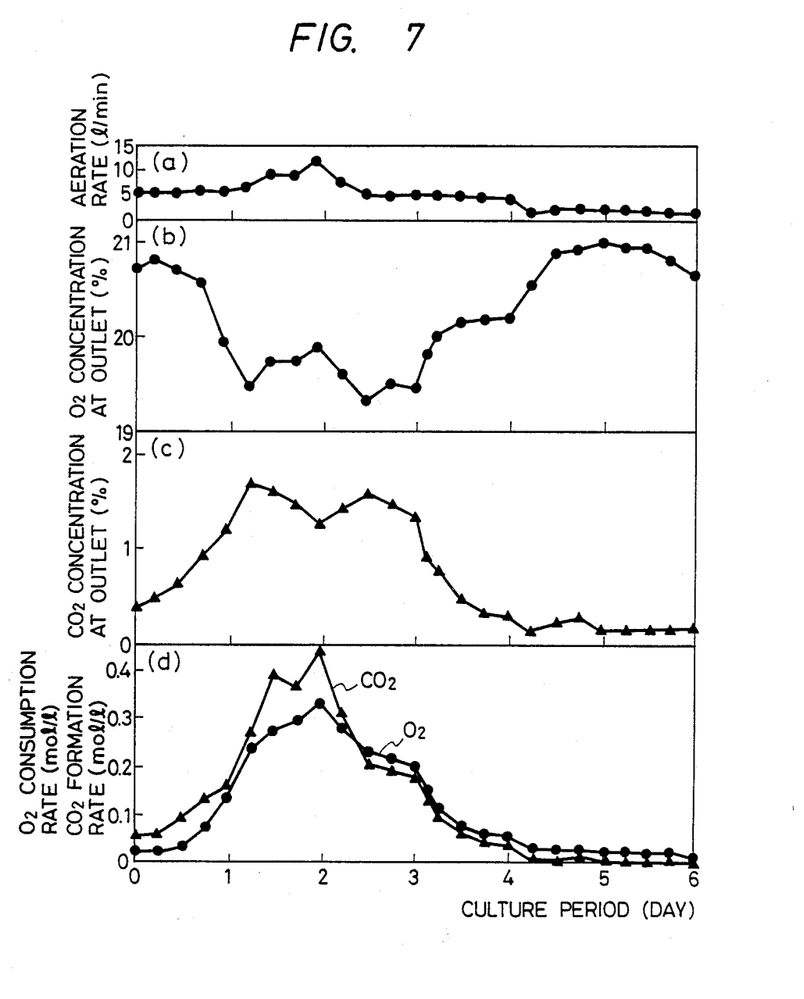

FIG. 5 shows a typical apparatus required in this embodiment. A medium and a seed culture are introduced into a culture tank 1 and a genetic recobminant bacterium is cultured therein with blowing air through a conduit 7 into the culture tank 1 and agitating the culturing broth with an agitator 2. During this period, the amount of oxygen at the inlet is determined with an computer 4 from the data obtained from a gas meter 5 and an oxygen analyzer 6 each equipped on the conduit 7, while the amounts of oxygen and carbon dioxide at the outlet are determined similarly with the computer 4 based on the data obtained from a gas meter 10, an oxygen analyzer 11 and a carbon dioxide analyzer 12, each equipped on a conduit 13 and RQ is further determined therefrom. When RQ shows a rapid increase, a signal from the control computer 4 actuates a substrate feeding pump 8, thus adding IA and casamino acids from a substrate tank 3 to the culture tank 1 through a conduit 9. When RQ shows a rapid increase again, the culture is terminated and cells are recovered from the culture broth and ground to isolate and purify β-gal accumulated therein.

When the supply gas is not air but pure oxygen, the oxygen analyzer 6 is unnecessary, and when it is a gas containing carbon dioxide, it is preferable to employ also a carbon dioxide analyzer.

As the oxygen analyzer, a membrane-type oxygen sensor and a dumbbell-shaped magnetic analyzer, as the carbon dioxide analyzer, an infrared absorption analzyer and as the flow meter, a thermal mass flow meter can be used, respectively.

Examples of preferred substrate are glucose, casamino acids and mixtures thereof.

When substrate (nutrients) and inducer are used together, it is preferable to add both the substances at the same time.

As a second embodiment of the present invention, a method for producing an antibiotic as a metabolite by Streptomyces griseus similar to streptomycin (SM) fermentation is described hereunder.

There have been examined various substrates to be fed during SM fermentation and it is found that glucose is effective. Subsequently the appropriate period of feeding glucose with the use of culture flasks is studied. Table 1 shows the result.

TABLE 1

| Feeding period | SM production (mg/l) |
|---|---|
| 1st day of culture | 45 |
| 2nd day of culture | 29 |
| 5th day of culture | 26 |
| control | 36 |

Glucose is added on the first, second and fifth days of the culture each to give an increase by 10 g/l. No significant effect is observed in each case.

Then, on the assumption that it might be effective to add glucose after the SM production reaches a maximum, glucose is added on the 2.5th day of the culture to give increases by 5, 10 and 20 g/l. Table 2 shows the result.

TABLE 2

| Glucose feeding (g/l) | SM production (mg/l) |
|---|---|
| 5 | 74 |
| 10 | 97 |
| 20 | 74 |
| control | 65 |

Table 2 suggests that the feeding of glucose on the 2.5th day of the culture to give an increase in 10 g/l would bring about an increase in the amount of the SM product by 1.5 times.

FIGS. 6(a) to (c) and FIGS. 7(a) to (d) show the result of SM fermentation which is carried out with an automatically controlled culture apparatus comprising a 50 l culture tank to examine when glucose should be added. On the second day of the culture when the amount of the SM produced reaches a peak, the oxygen consumption rate and the carbon dioxide formation rate each shows a rapid decrease. The glucose concentration at this point is 10 g/l which indicates that approximately 50% of the initial amount of glucose remains. Nevertheless such a phenomenon is observed presumably because the metabolism of the SM-producing bacterium seems to alter its direction from SM production to something else. Such rapid changes in oxygen consumption and carbon dioxide formation rates have been found by the inventors for the first time. Thus, the SM proructivity by feeding glucose under the guidance of these changes has been improved.

The oxygen consumption rate is determined by subtracting the amount of oxygen (mol/h) in the discharge gas from that (mol/h) in the supply gas, while the carbon dioxide formation rate is determined by subtracting the amount of carbon dioxide (mol/h) in the supply gas from the (mol/h) in the discharge gas. When the amount of the supply gas is constant, changes in the oxygen and carbon dioxide concentrations in the discharge gas may be employed as indications as such.

Sugars such as fructose and amino acids may be fed as a substrate similar to glucose.

In performing this embodiment, a preliminary culture test may be carried out by using the same substrate to be used and the same strain or cells to be cultured to thereby determine the point at which the oxygen consumption and/or carbon dioxide formation rates rapidly change with the particular combination of the conditions and the actual feeding point may be determined based on the result of this preliminary test.

The following examples corresponding to the above embodiments, respectively, will be given.

EXAMPLE 1

Strain: An E. coli HB101 strain carrying a complex plasmid pTREZ1. This strain originates from E. coli k-12 strain and has been known as a typical host in genetic recombination. Its genetic type is represented by $F^-$ (F factor defective), hsd S20 ($r_B^-$, $m_B^-$), recA 13 ara-14, proA 2, lacY1, galK2, rpsL20(Sm$^r$), xyl-5, mtl-1, supE44 and $\lambda^-$ ($\lambda$phage defective).

Medium: An M9-casamino acid medium (pH 7.0) comprising 1 g of $NH_4Cl$, 6 g of $Na_2HPO_4$, 3 g of $KH_2PO_4$, 5 g of NaCl, 0.1 g of $MgSO_4 \cdot 7H_2O$, 15 mg of $CaCl_2 \cdot 2H_2O$, 5 g of glucose, 2.5 g of casamino acids, 0.1 g of thiamin, 0.1 g of proline and 1 l of distilled water. 50 μg/ml of ampicillin (Ap) was further added to this medium to thereby selectively grow the E. coli strain carrying the complex plasmid alone.

Culture condition: An E. coli strain carrying a complex plasmid (deposited in FRI as FERM BP 815; E. coli HB101 (pTREZ1)) was inoculated into 50 ml portions of an M9-casamino acid medium in eight shake flasks of 500 ml in volume and cultured therein under shaking with an stroke of 7 cm at 115 oscillations/min. and at 37° C. overnight. 100 ml portions of the cell culture were inoculated as a seed culture into 2 l of the M9-casamino acid medium in four jar fermenters of 5 l in volume and cultured therein. Two drops of a antifoam agent (Leocon 1750W: mfd. by The Lion Co., Ltd.) was added thereto. The culture was carried out at 37° C. and at pH 7.0 while mechanically agitating at 600 rpm with aerating at a rate of 2 l/min overnight. 8 l of this culture broth was inoculated into an automatically controlled culture apparatus of 50 l in volume and the M9-casamino acid medium was added thereto to give a total volume of 30 l. The same antifoam agent ae described above was added thereto and culture was performed at 37° C. and at pH 7.0 with aerating at a rate of 6 l/min and at a dissolved oxygen concentration of 3 mg/l while mechanically agitating at 150 to 400 rpm.

Figure 8:
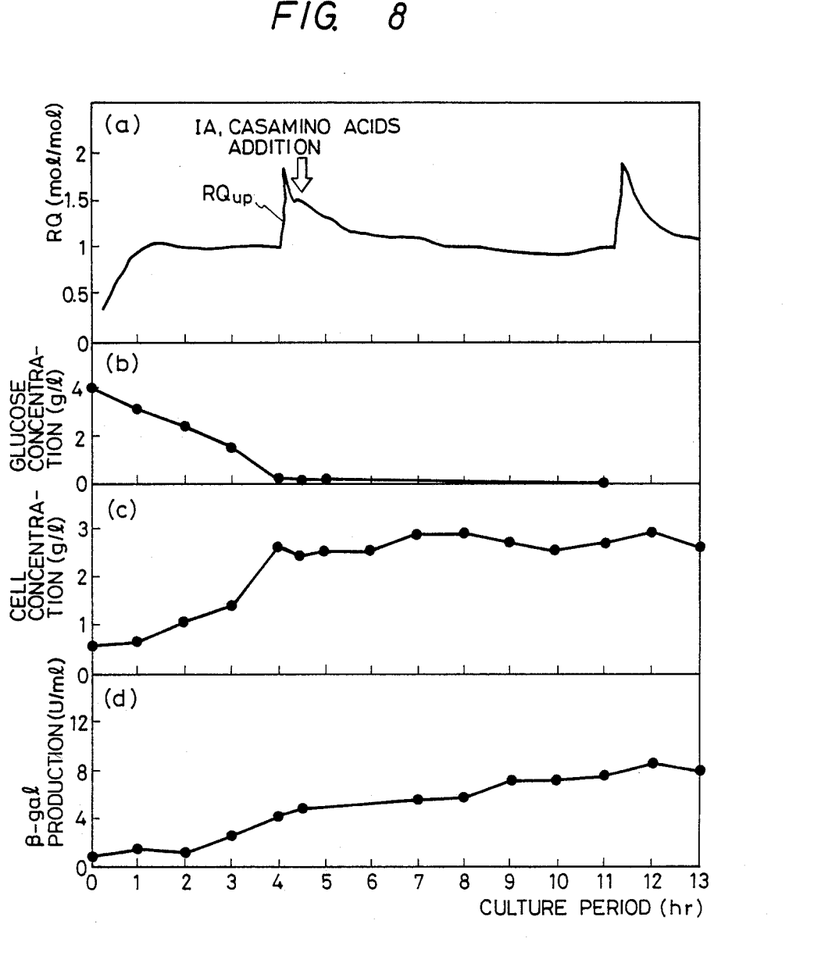
FIGS. 8 and 9 are graphs each showing the result of the practice of the culture control relating to examples of the present invention.

Results: As shown in FIG. 8, RQ showed a rapid increase approximately four hours after initiating the culture. Then 15 μg/ml of IA and 2.5 mg/ml of casamino acids were added. When RQ showed an increase, the cell concentration was 2.69 g/l while the amount of β-gal was 4.3 U/ml. RQ showed an increase again 11.5 hours after initiating the culture. At this point, the cell concentration was 2.66 g/l and the amount of β-gal was 8.3 U/ml. Thus the cell concentration showed little increase while the β-gal nearly doubled.

These results suggest that the yield of β-gal can be remarkably raised by adding IA and casamino acids under the guidance of RQ.

The culture may be terminated after RQ reaches the second peak.

As strain carrying a complex plasmid pTREZ1, an E. coli M 182 which originates from E. coli k-12 strain and lacks in β-gal gene on a chromosome, and whose genetic type is represented by Δ(lac IPOZY)X74, gal U, Str A, also can be used. In this case, medium and culture conditions are the same as above except that an E. coli strain carrying a complex plasmid (E. coli M182 (pTREZ1), deposited in FRI as FERM BP-816) is used in place of the above E. coli strain.

EXAMPLE 2

Strain: Streptomyces griseus HUT2247.

Composition of medium: 25 g of Glucose, 2 g of $(NH_4)_2SO_4$, 0.4 g of $KH_2PO_4$, 1 g of NaCl, 6 g of $K_2SO_4$, 0.2 g of $MgSO_4.7H_2O$, 0.01 g of $FeSO_4.7H_2O$, 0.05 g of $ZnSO_4.7H_2O$, 7 g of L-asparagine, 2 g of $CaCO_3$ and 1 l of distilled water (pH 7.0).

Culture condition: 30 l of the medium was introduced in a culture tank of 50 l in volume and 600 ml of a seed culture previously cultured under shaking for 48 hours was added thereto. The culture was carried out at 28° C. and at pH 6.7 while maintaining the amount of the gas at the inlet at 8 l/min. The mechanical agitation rate was changed to 140 to 245 rpm to thereby control the dissolved oxygen concentration above 4.5 mg/l.

Figure 9:
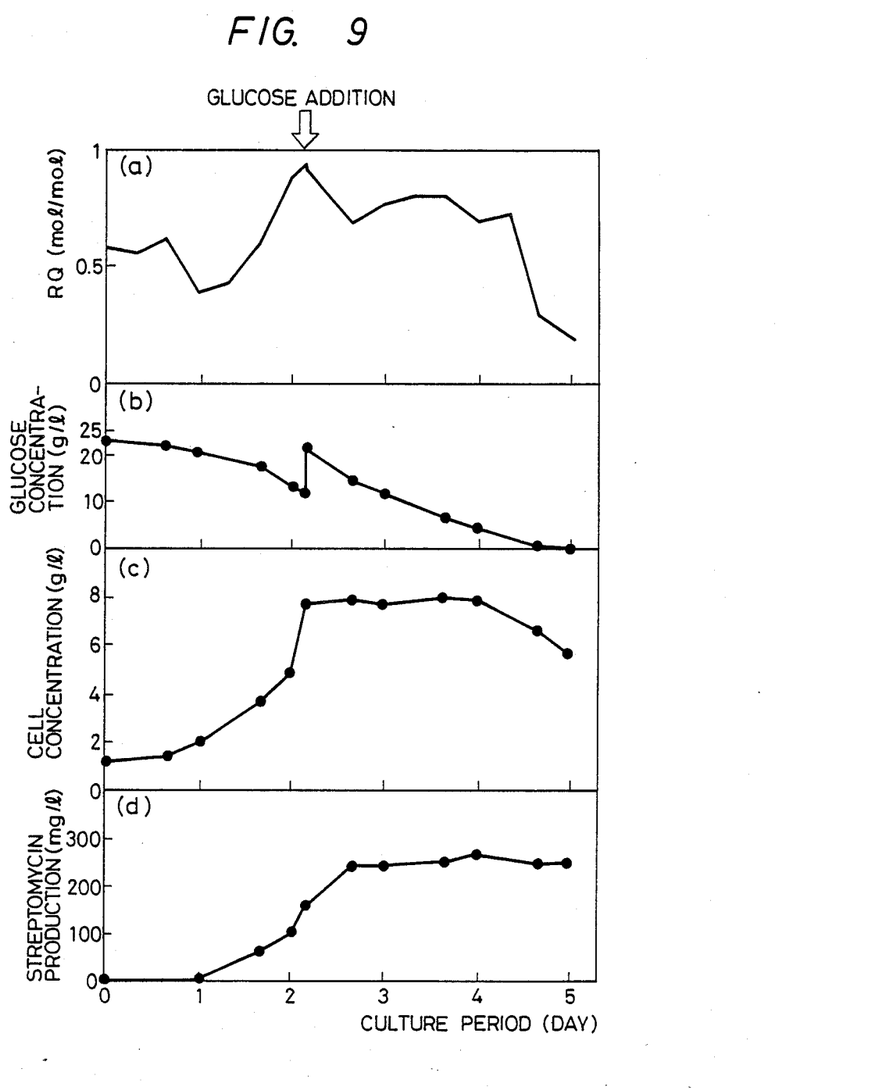

Results: As shown in FIG. 9, RQ remained 0.5 mol/-mol during the early stage of the culture, began to rise from the latter half of the first day and reached the maximum 2.2 days after initiating the culture. Then 1 l of glucose (300 g/l) which was a substrate was added thereto. At this point, the cell concentration reached the maximum and 11.5 g/l of glucose still remained. The yield of streptomycin was 155 mg/l at this point and reached 265 mg/l (i.e. 1.7 times as high as the former) after adding glucose and subsequently culturing for three days. After the fourth day of the culture, RQ fell because of bacteriolysis, which roughly coincided with the consumption of the glucose in the medium.

Thus streptomycin fermentation may be effectively controlled under the guidance of RQ.

As described above, the present invention is effective in efficiently producing metabolite(s) by cell culture in an industrial scale.

What is claimed is:

1. A method of controlling culture wherein cells are aerobically cultured in a culture broth to produce metabolite, comprising the steps of:
   detecting a first parameter based on the amount of carbon dioxide evolved by the cells;
   detecting a second parameter based on the amount of oxygen consumed by the cells;
   calculating the ratio of said first parameter and said second parameter thereby obtaining a value representing a respiratory quotient of the cells; and
   adding a substrate to the culture broth under the guidance of said value in a period of time from a rapid rise of said value until immediately after termination of said rise and in a period when initially fed substrate is reduced to a substrate concentration at which concentration of the cells reaches about a maximum, said substrate being at least one selected from the group consisting of casamino acid, glucose, amino acids other than trytophan and yeast extract.

2. A method of controlling culture as set forth in claim 1, wherein said cells are microbial cells.

3. A method of controlling culture as set forth in claim 2, wherein said microbial cells are genetic recombinant bacterial cells.

4. A method of controlling culture as set forth in claim 1, wherein said steps of detecting said first and second parameters and said step of adding a substrate are carried out on-line.

5. A method of controlling culture as set forth in claim 2, further comprising the step of judging the end point of growth of the cells under the guidance of a second rapid rise in a value representing said respiratory quotient appearing secondarily after the addition of said substrate and thereafter terminating culture.

6. A method of controlling culture wherein cells are aerobically cultured in a culture broth to produce metabolite, comprising the steps of:
   detecting an amount of carbon dioxide discharged by the cells;
   detecting an amount of oxygen consumed by the cells;
   calculating a respiratory quotient from the detected amounts of carbon dioxide and oxygen; and
   feeding at least one of a substrate and an inducer into the culture broth containing said cells in a period from a first rapid rise of said respiratory quotient, until immediately after termination of the first rapid rise, said first rapid rise taking place in a period when initially fed substrate is reduced to a substrate concentration at which cell concentration reaches about a maximum thereof; said substrate being at least one selected from the group consisting of casamino acid, glucose, amino acids other than trytophan and yeast extract.

7. A method of controlling culture as set forth in claim 6, wherein the culture is terminated, based on the detection of a second rapid rise of said respiratory quotient which occurs after said period.

8. A method of controlling culture as set forth in claim 6, wherein said step of detecting carbon dioxide and said step of detecting oxygen include detection of a flow rate and carbon dioxide and oxygen concentrations of a gas introduced into a culture tank in which the cell culture is effected, and detection of a flow rate and oxygen and carbon dioxide concentrations of a gas discharged from said culture tank.

9. A method of controlling culture as set forth in claim 6 wherein said cells are microbial cells.

10. A method of controlling culture as set forth in claim 9, wherein said microbial cells are genetic recombinant bacterial cells.

11. A method of controlling culture, wherein cells are aerobically cultured to produce metabolite, comprising the steps of:
    determining strain, medium and culture conditions which are necessary to produce metabolite;
    predetermining a point in time of a rapid rise in the respiratory quotient of the cells to be cultured under said determined conditions which takes place around the time at which concentration of the cells reaches about a maximum thereof;
    detecting a first parameter based on the amount of carbon dioxide evolved by the cells being cultured;
    detecting a second parameter based on the amount of oxygen consumed by said cells;
    calculating the respiratory quotient from said first and second parameters;
    detecting a respiratory quotient rapid rise occurring around said point in time of said predetermined rapid rise after initiating the culture; and
    adding a substrate effective to cause the cells to produce metabolite to the culture broth after the detection of said respiratory quotient under rapid rise.

12. A method of controlling culture as set forth in claim 11, wherein said step of adding a substrate is conducted in a period from the initiation of said respiratory quotient rapid rise until immediately after said respiratory quotient rapid rise.

13. A method of controlling culture as set forth in claim 11, further including the steps of detecting another rapid rise of respiratory quotient which occurs secondarily after the substrate addition, and detecting the termination of the culture thereby.

14. A method of controlling culture, as set forth in claim 11, wherein said inducer is added to the culture broth together with a substrate.

15. A method of controlling culture as set forth in claim 11, wherein said cells are microbial cells.

16. A method of controlling culture as set forth in claim 15, wherein said microbial cells are genetic recombinant bacterial cells.

17. A method of controlling culture as set forth in claim 11, wherein said step of predetermining a rapid rise in the respiratory quotient includes a preliminary experiment conducted under said conditions of culture.

* * * * *